(12) United States Patent
Kemp et al.

(10) Patent No.: US 11,744,649 B2
(45) Date of Patent: Sep. 5, 2023

(54) METHOD AND APPARATUS FOR IDENTIFICATION OF MULTIPLE NAVIGATED INSTRUMENTS

(71) Applicant: Medtronic Navigation, Inc., Louisville, CO (US)

(72) Inventors: Justin Kemp, Erie, CO (US); Victor D. Snyder, Erie, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 160 days.

(21) Appl. No.: 17/116,050

(22) Filed: Dec. 9, 2020

(65) Prior Publication Data
US 2021/0085405 A1 Mar. 25, 2021

Related U.S. Application Data

(63) Continuation of application No. 14/753,885, filed on Jun. 29, 2015, now Pat. No. 10,898,271.

(51) Int. Cl.
*A61B 34/20* (2016.01)
*A61B 90/92* (2016.01)
(Continued)

(52) U.S. Cl.
CPC .............. *A61B 34/20* (2016.02); *A61B 34/25* (2016.02); *A61B 90/37* (2016.02); *A61B 90/92* (2016.02);
(Continued)

(58) Field of Classification Search
CPC ......... A61B 34/00; A61B 34/20; A61B 34/25; A61B 2034/256; A61B 90/37; A61B 90/90; A61B 90/92; A61B 90/94; A61B 90/96; A61B 90/98; A61B 2090/3904; A61B 2090/3916; A61B 2090/3937; A61B 2090/3954; A61B 2090/3983; A61B 2034/2055; A61B 2034/2068; A61B 2034/2074; A61B 2034/25; A61B 2034/2046; A61B 2034/2048; A61B 2034/2051; A61B 2034/2059; A61B 2034/107
(Continued)

(56) References Cited

U.S. PATENT DOCUMENTS 5,603,318 A 2/1997 Heilbrun et al.
6,374,134 B1 4/2002 Bladen et al.
(Continued)

FOREIGN PATENT DOCUMENTS

EP 2046538 A2 4/2009
WO 0139683 A1 6/2001
WO 2004030560 A2 4/2004

OTHER PUBLICATIONS

European Office Action regarding European Patent Application No. 16738323.1, dated Jan. 31, 2020.
(Continued)

*Primary Examiner* — Carolyn A Pehlke
(74) *Attorney, Agent, or Firm* — Harness, Dickey & Pierce, P.L.C.

(57) ABSTRACT

A tracking system can be used to track a plurality of tracking devices. A representation of at least two instruments may be displayed relative to image data. The representation is customizable to distinguish between the at least two instruments.

18 Claims, 5 Drawing Sheets

(51) Int. Cl.
    *A61B 34/00*     (2016.01)
    *A61B 90/00*     (2016.01)
    *A61B 90/98*     (2016.01)

(52) U.S. Cl.
    CPC .............. *A61B 90/98* (2016.02); *A61B 90/39* (2016.02); *A61B 2034/2051* (2016.02); *A61B 2034/2055* (2016.02); *A61B 2034/256* (2016.02); *A61B 2090/376* (2016.02); *A61B 2090/3983* (2016.02)

(58) Field of Classification Search
    USPC ....................................................... 600/424
    See application file for complete search history.

(56) References Cited

U.S. PATENT DOCUMENTS

| | | | |
|---|---|---|---|
| 6,747,539 | B1 | 6/2004 | Martinelli |
| 6,940,941 | B2 | 9/2005 | Gregerson et al. |
| 7,001,045 | B2 | 2/2006 | Gregerson et al. |
| 7,108,421 | B2 | 9/2006 | Gregerson et al. |
| 7,188,998 | B2 | 3/2007 | Gregerson et al. |
| 7,763,035 | B2 | 7/2010 | Melkent et al. |
| 7,835,778 | B2 | 11/2010 | Foley et al. |
| 7,996,064 | B2 | 8/2011 | Simon et al. |
| 8,467,853 | B2 | 6/2013 | Hunter et al. |
| 8,644,907 | B2 | 2/2014 | Hartmann et al. |
| 9,042,513 | B2 | 5/2015 | Shi et al. |
| 10,898,271 | B2 | 1/2021 | Kemp et al. |
| 2005/0085714 | A1 | 4/2005 | Foley et al. |
| 2006/0036241 | A1 | 2/2006 | Siegal |
| 2006/0217733 | A1 | 9/2006 | Plassky et al. |
| 2006/0258938 | A1 | 11/2006 | Hoffman et al. |
| 2008/0004603 | A1* | 1/2008 | Larkin ................ B25J 9/1694 606/1 |
| 2008/0185430 | A1 | 8/2008 | Goldbach |
| 2008/0200927 | A1 | 8/2008 | Hartmann et al. |
| 2010/0228249 | A1 | 9/2010 | Mohr et al. |
| 2012/0097178 | A1 | 4/2012 | Helm et al. |
| 2012/0099768 | A1 | 4/2012 | Helm et al. |
| 2014/0055489 | A1 | 2/2014 | Itkowitz et al. |
| 2014/0313193 | A1 | 10/2014 | Helm et al. |
| 2014/0314199 | A1 | 10/2014 | Shi et al. |
| 2015/0150641 | A1 | 6/2015 | Daon et al. |
| 2016/0374764 | A1 | 12/2016 | Kemp et al. |
| 2017/0027650 | A1 | 2/2017 | Merck et al. |

OTHER PUBLICATIONS

International Preliminary Report on Patentability dated Jan. 11, 2018 in corresponding International Application No. PCT/US2016/039800.

International Search Report and Written Opinion dated Sep. 28, 2016 for PCT/US2016/039800 claiming benefit of U.S. Appl. No. 14/753,885, filed Jun. 29, 2015.

Kantelhardt, Sven Rainer, Ramon Martinez, Stefan Baerwinkel, Ralf Burger, Alf Giese, and Veit Rohde. "Perioperative course and accuracy of screw positioning in conventional, open robotic-guided and percutaneous robotic-guided, pedicle screw placement." European Spine Journal 20, No. 6 (2011): 860-868.

* cited by examiner

METHOD AND APPARATUS FOR IDENTIFICATION OF MULTIPLE NAVIGATED INSTRUMENTS

CROSS-REFERENCE TO RELATED APPLICATIONS

This application is a continuation of U.S. application Ser. No. 14/753,885 filed on Jun. 29, 2015. The entire disclosure of the above application is incorporated herein by reference.

FIELD

The subject disclosure relates generally to a display system, in particularly to a display and selection system for a surgical system.

BACKGROUND

This section provides background information related to the present disclosure which is not necessarily prior art.

In a surgical procedure, a portion of a patient may be operated on by a surgeon. During the surgical procedure the operation may require the use of various instruments to be positioned within portions of the anatomy. For example, during a spinal fusion procedure various instruments including a tap and/or a screwdriver may be inserted into portions of the anatomy to perform a portion of the procedure. A spinal fusion procedure is generally understood in the art and may include the tapping of bores in vertebrae and placing of screws within the bores.

The procedure may include an augmentation of the anatomy, such as movement or augmentation of bone, insertion of implantable devices, or other appropriate procedures. A surgeon can perform the procedure on the patient based on images of the patient, which can be acquired using an x-ray imaging system. The images may be acquired prior to or during the procedure. The imaging system may be, for example, acquired with an O-Arm® medical imaging system such as those sold by Medtronic, Inc. or C-Arm imaging system. The images may be volumetric, fluoroscopic, and/or radiographic images depending on an operating mode of the imaging system.

SUMMARY

This section provides a general summary of the disclosure, and is not a comprehensive disclosure of its full scope or all of its features.

A procedure may include an operation performed on a selected subject. The procedure may require the use of various instruments to perform the operation on the subject. Further, multiple instruments may be used simultaneously during the procedure. The subject may include a living subject, such as a human patient, an animal patient, or other living patient. The subject may also include an inanimate subject, such as a motor vehicle or computer system. In various procedures, a portion of a tool or instrument may be obfuscated or covered by the portion of the subject.

According to various embodiments, a tracking system can be used to track a tracking device. Alone or in combination with a navigation system, a location of at least a portion of the instrument may be illustrated relative to a portion of the subject. The tracking system may be able to track a plurality of instruments substantially simultaneously and illustrate all the instruments simultaneously on one or more display. Further the system, including the tracking system and navigation system, may be able to differentiate between the plurality of instruments and illustrate the plurality of instrument to be distinguishable from another. For example, a display may visually distinguish one instrument from another instrument although they are substantially identical visually on the display. For example, a plurality of screwdrivers may be illustrated on a display that may have substantially identical features (e.g. a driving tip) but may be distinguished with various indicia on the display device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
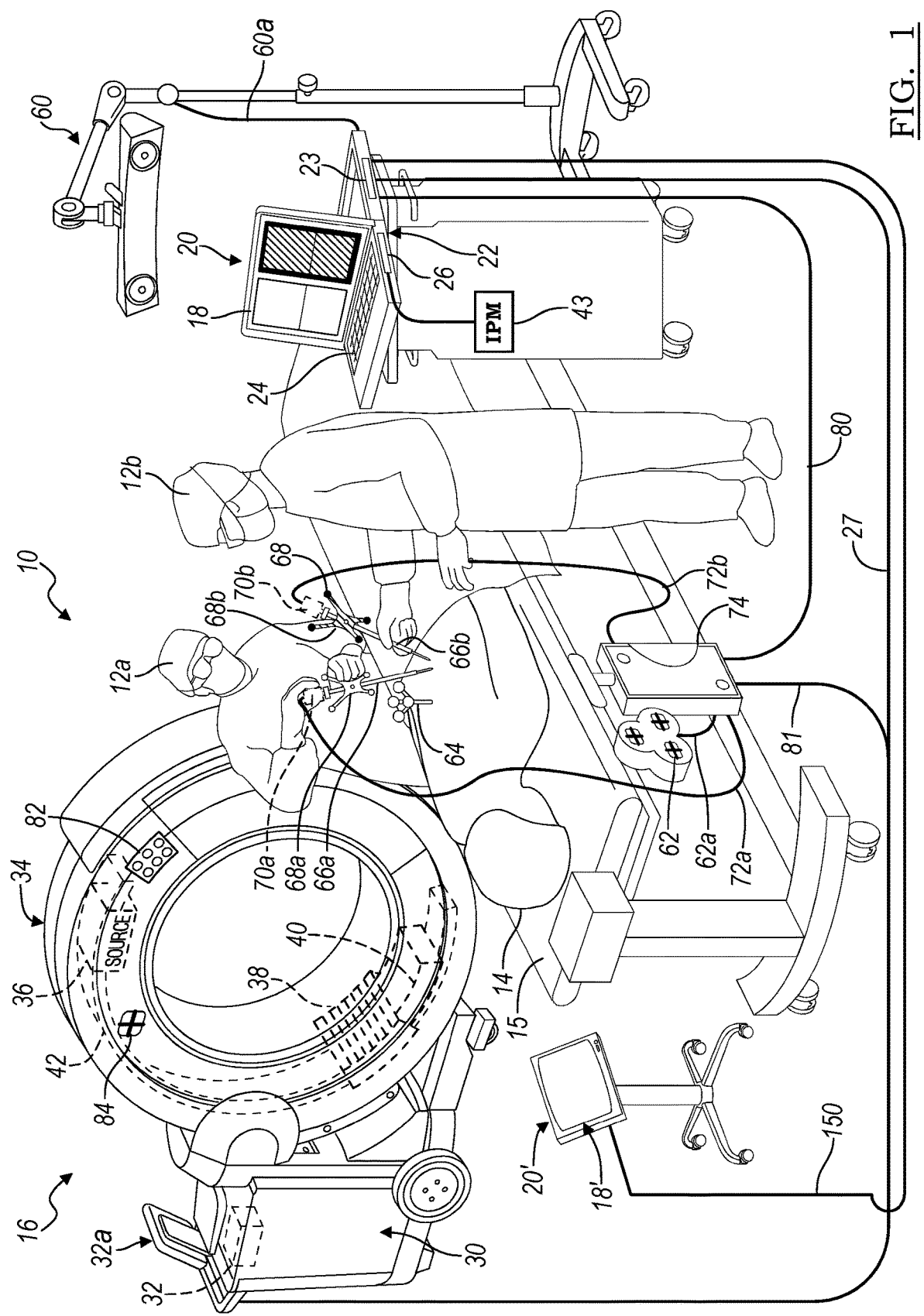
FIG. 1 is an environmental view of at least a portion of a suite including an imaging system, a tracking system, and a navigation system in accordance with an embodiment of the present disclosure.

The following description is merely exemplary in nature. It should be understood that throughout the drawings, corresponding reference numerals indicate like or corresponding parts and features. As indicated above, the present teachings are directed toward system that is able to track more than one instrument and distinguish them on a display. For example, more than one surgical instrument may be tracked during a surgical procedure. The several instruments may be illustrated in a distinguishable manner on a display device, such as a monitor. It is understood that the tracking system may be applied to non-surgical applications for tracking more than one instrument used during various repair or maintenance procedures on machinery, devices, etc.

FIG. 1 shows an operating theatre (or inside of an operating room) 10 and a first user 12a (e.g., a physician) and a second user 12b (e.g., a physician) performing a procedure on a subject (e.g., a patient) 14 positioned on a table or surface 15. In performing the procedure, the users 12a, 12b may use an imaging system 16 to acquire image data of the patient 14. The image data acquired of the patient 14 can include two-dimensional (2D) or three-dimensional (3D) images. Models, such as surface renderings or volumetric models, may be generated using the acquired image data. The model can be a three-dimensional (3D) volumetric model generated based on the acquired image data using various techniques, including algebraic iterative techniques. The image data (designated 18) can be displayed on a display device 20, and additionally, may be displayed on a display device 32a associated with an imaging computing system 32. The displayed image data 18 may include 2D images, 3D images, and/or a time changing 3D (also referred to as 4D) images. The displayed image data 18 may also include acquired image data, generated image data, and/or a combination of the acquired and generated image data.

Image data acquired of a patient 14 may be acquired as 2D projections. The 2D projections may then be used to reconstruct 3D volumetric image data of the patient 14. Also, theoretical or forward 2D projections may be generated from the 3D volumetric image data. Accordingly, image data may be used to provide 2D projections and/or 3D volumetric models.

The display device 20 may be part of a computing system 22. The computing system 22 may include a memory system 23 including one or a variety of computer-readable media. The computer-readable media may be any available media that is accessed by the computing system 22 and may include both volatile and nonvolatile media, and removable and non-removable media. By way of example, the computer-readable media may include computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors may include multiple-processing core processors, microprocessors, etc.) that may be incorporated with the computing system 22. The input device 24 may include any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 may include a touchpad or tablet computing device and may be integrated within or be part of the imaging computing system 32. A connection may be provided between the computing system 22 and the display device 20 for data communication to allow driving the display device 20 to illustrate the image data 18. Further, a communication line 27 may be provided between the imaging computer system 32 and the computer system 22.

The imaging system 16 may be an O-Arm® imaging system, a C-Arm imaging system, or other suitable imaging system. The O-Arm® imaging system can include the O-Arm® imaging system sold by Medtronic, Inc. having a place of business in Colorado, USA. The imaging system may further include, in various embodiments, the imaging systems described in U.S. Pat. App. Pub. Nos. 2012/0099768, 2012/0097178, 2014/0313193, and 2014/0314199 all of which are incorporated herein by reference.

In various embodiments, the imaging system 16 may include a mobile cart 30, the imaging computing system 32 and a gantry 34 (or x-ray scanner gantry). The gantry 34 may house and includes an x-ray source 36, a collimator (not shown), one or both of a multi-row detector 38 and a flat panel detector 40, and a rotor 42. With reference to FIG. 1, the mobile cart 30 may be moved from one operating theater or room to another and the gantry 34 may be moved relative to the mobile cart 30. This allows the imaging system 16 to be mobile and used for various procedures without requiring a capital expenditure or space dedicated to a fixed imaging system. Although the gantry 34 is shown as being mobile, the gantry 34 may not be connected to the mobile cart 30 and may be in a fixed position.

The gantry 34 may define an isocenter of the imaging system 16. In this regard, a centerline Cl through the gantry 34 defines an isocenter or center of the imaging system 16. The gantry 34 may include a gantry similar to that disclosed in U.S. Pat. Nos. 7,188,998; 7,108,421; 7,001,045; and 6,940,941 all incorporated herein by reference. Generally, the patient 14 can be positioned along the centerline Cl of the gantry 34, such that a longitudinal axis of the patient 14 is aligned with the isocenter of the imaging system 16.

The imaging computing system 32 may control the movement, positioning and adjustment of the multi-row detector 38, the flat panel detector 40 and the rotor 42 independently to enable image data acquisition via an image processing module 43 of the processor 26. The processed images may be displayed on the display device 20.

The imaging system 16 may be precisely controlled by the imaging computing system 32 to move the source 36, collimator, the multi-row detector 38 and the flat panel detector 40 relative to the patient 14 to generate precise image data of the patient 14. In addition, the imaging system 16 may be connected with the processor 26 via the connection 27 which includes a wired or wireless connection or physical media transfer from the imaging system 16 to the processor 26. Thus, image data collected with the imaging system 16 may also be transferred from the imaging computing system 32 to the computing system 22 for navigation, display, reconstruction, etc.

The imaging system 16 may also be used during an unnavigated or navigated procedure. In a navigated procedure, a localizer may be used to determine location of tracked instruments and portions. The tracked portions may include the patient 14, the imaging system 16, the users 12a, 12b, etc. The localizer may be one or both of an optical localizer 60 or an electromagnetic localizer 62. The localizer may further include an ultrasound localizer, a radar localizer, etc. The localizer may be used to generate a field or receive or send a signal within a navigation domain relative to the patient 14. If desired, the components associated with performing a navigated procedure (e.g. the localizer) may be integrated within the imaging system 16. The navigated space or navigational domain relative to the patient 14 may be registered to the image data 18 to allow registration of a navigation space defined within the navigational domain and an image space defined by the image data 18. A patient tracker (or a dynamic reference frame) 64 may be connected to the patient 14 to allow for a dynamic registration and maintenance of the registration of the patient 14 to the image data 18.

One or more instruments may be tracked within the navigational domain, including relative to the patient 14. Instruments may include a first instrument 66a and a second instrument 66b that may then be tracked relative to the patient 14 to allow for a navigated procedure. The instruments 66a, 66b may include respective optical tracking devices 68a, 68b (including active or passive tracking devices, including those discussed herein) and/or an electromagnetic tracking devices 70a, 70b (shown in phantom) to allow for tracking of the instruments 66a, 66b with either or both of the optical localizer 60 or the electromagnetic localizer 62. The instruments 66a, 66b may include communication lines 72a, 72b with a navigation interface device (NID) 74. The NID 74 may communicate with the electromagnetic localizer 62 and/or the optical localizer 60 directly or via the processor 26 via communication lines 60a and 62a respectively. The NID 74 may communicate with the processor 26 via a communication line 80. The imaging system 16 may also communicate with the NID 74 via a communication line 81. The connections or communication lines can be wire based as shown or the corresponding devices may communicate wirelessly with each other.

The localizer 60 and/or 62 along with the selected tracking devices may be part of a tracking system that tracks the instruments 66a, 66b relative to the patient 14 to allow for illustration of the tracked location of the instrument 66 relative to the image data 18 for performing a procedure. The tracking system alone or in combination with a navigation system is configured to illustrate a tracked location (including a tracked 3D position (i.e. x,y,z coordinates) and one or more degrees of freedom of orientation (i.e. yaw, pitch, and roll)) relative to the image data 18 on the display 20. Various tracking and navigation systems include the StealthStation® surgical navigation system sold by Medtronic, Inc. and those disclosed in U.S. Pat. Nos. 8,644,907; 8,467,853; 7,996,064; 7,835,778; 7,763,035; 6,747,539; and 6,374,134, all incorporated herein by reference. As is generally understood, the processor 26 may execute selected instructions to illustrate a representation (e.g. an icon) of the tracked portion relative to the image data 18. As discussed further herein, according to various embodiments, two or more icons may be illustrated relative to the image data and distinguished from one another on the display for identification of the selected instrument, such as the first instrument 66a or the second instrument 66b.

The instruments 66a, 66b may be interventional instruments and/or implants. Implants may include a ventricular or vascular stent, a spinal implant, neurological stent or the like. The instruments 66a, 66b may be an interventional instrument such as a deep brain or neurological stimulator, an ablation device, or other appropriate instrument. Tracking the instruments 66a, 66b allows for viewing the location of the instruments 66a, 66b relative to the patient 14 with use of the registered image data 18 and without direct viewing of the instruments 66a, 66b within the patient 14. For example, the instruments 66a, 66b may be graphically illustrated as an icon, as discussed further herein, superimposed on the image data 18.

Further, the imaging system 16 may include a tracking device, such as an optical tracking device 82 or an electromagnetic tracking device 84 to be tracked with a respective optical localizer 60 or the electromagnetic localizer 62. The tracking devices 82, 84 may be associated directly with the source 36, multi-row detector 38, flat panel detector 40, rotor 42, the gantry 34, or other appropriate part of the imaging system 16 to determine the location of the source 36, multi-row detector 38, flat panel detector 40, rotor 42 and/or gantry 34 relative to a selected reference frame. As illustrated, the tracking devices 82, 84 may be positioned on the exterior of the housing of the gantry 34. Accordingly, portions of the imaging system 16 including the instruments 66a, 66b may be tracked relative to the patient 14 to allow for initial registration, automatic registration, or continued registration of the patient 14 relative to the image data 18.

As discussed above, the first user 12a and the second user 12b, can perform a procedure on the patient 14. Both of the users 12a, 12b may position the respective instruments 66a, 66b relative to, such as within, the patient 14. For example, the instruments 66a, 66b can include an awl cap, a probe, a screwdriver, an instrument to hold or position one or more screws, a rod, or the light. It is understood that both instruments may be used simultaneously, i.e. both of the instruments are tapping or boring holes at the same time. It is also understood, however, that simultaneous use or operation of the instruments may be be different in time by a selected amount. For example, the user 12a may initiate boring a hole and then the second used 12b may initiate boring a hole. Both instruments 66a and 66b, however, may be tracked with the respective tracking devices e.g. 68a and 68b. Thus, operation of the instruments 66a, 66b may be simultaneous or substantially simultaneous without being operated at the same instant in time.

An operative or operating portion (which may be a detachable portion) of the instruments 66a, 66b may be positioned subdermally and transdermally. In various embodiments, the portion of the instruments in 66a, 66b positioned subdermally are positioned through a small incision or stab wound formed on or in the patient 14. Therefore, direct viewing, such as with visual viewing directly by the users 12a, 12b may be substantially hindered and/or impossible due to the overlayment of soft tissue including dermis, muscle, and the like. Therefore, the tracking and navigation systems, as discussed above, can be used to display representations of the instruments 66a, 66b relative to the image data 18 on display 20.

Figure 2A:
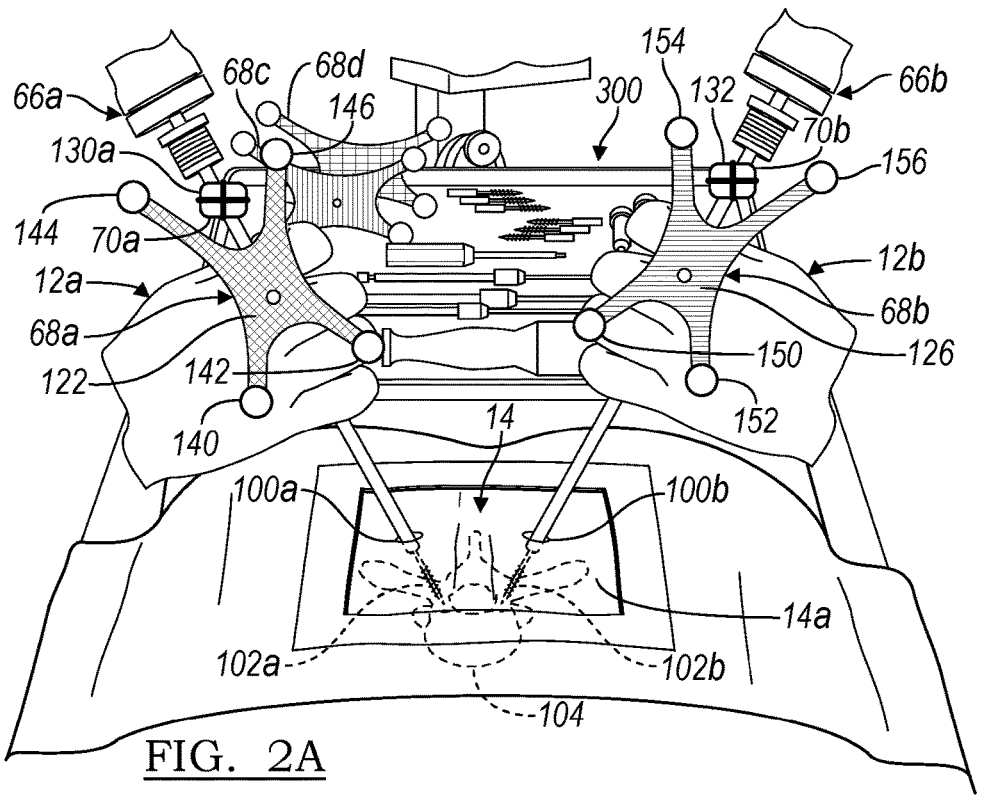
FIG. 2A is an environmental view of a procedure occurring with two instruments, according to various embodiments.
Figure 2B:
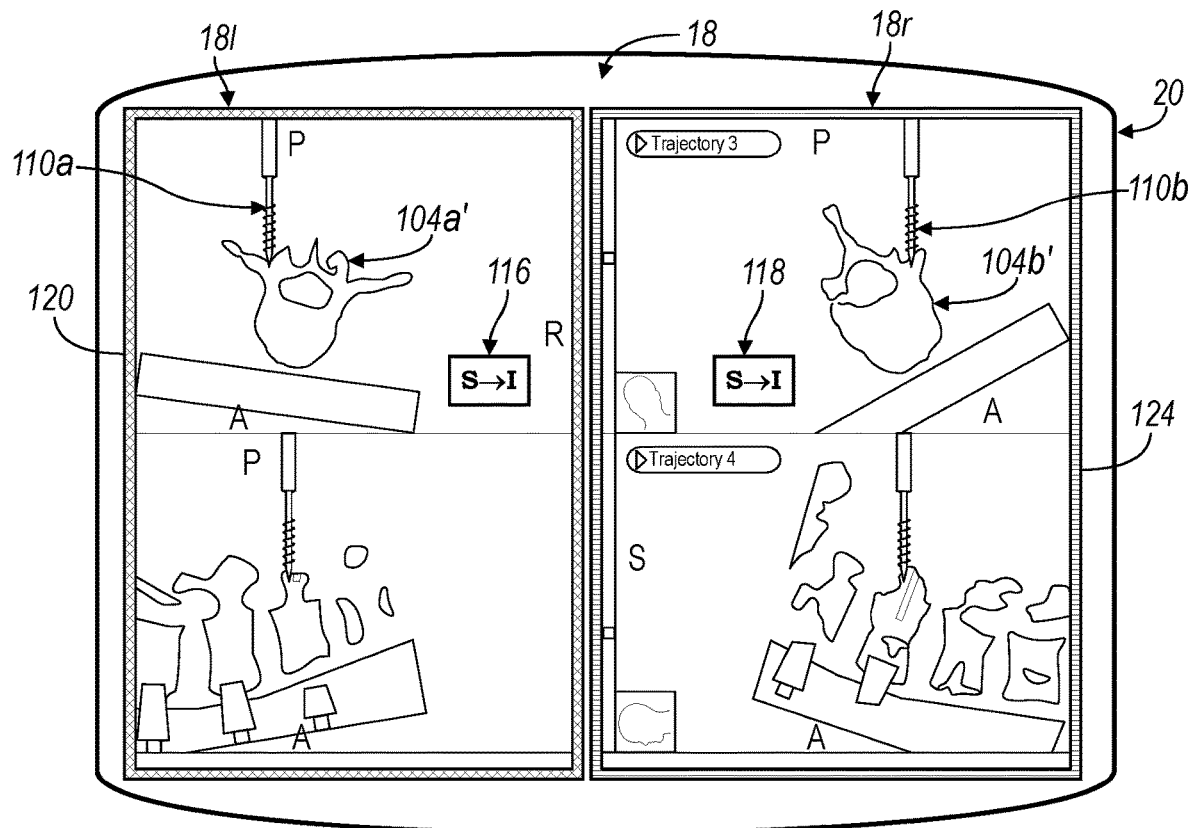
FIG. 2B is a screenshot of a display device displaying the two instruments with a visual distinction, according to various embodiments.

With continuing reference to FIG. 1, and additional reference to FIG. 2A and FIG. 2B, the two instruments 66a and 66b can be manipulated by the respective users 12a and 12b relative to the patient 14, is specifically illustrated in FIG. 2A. For example, a first incision 102a may be made for passing the first instrument 66a into the patient 14, while a second incision 102b may be made to pass the second instrument 66b into the patient 14. Each of the instruments 66a, 66b may include taps or may be formed to include a tapping portion 102a and 102b, respectively. The tapping portions 102a, 102b may be used to tap bores or holes in a vertebra 104. While the following discussion may relate to positioning implants within the vertebra 104, such as screws for a spinal fusion, it is understood that the subject disclosure relates to various procedures in addition to or alternatively to performing a spinal fusion.

The portions of the instruments 66a, 66b, including the tapping portions 102a, 102b, may generally not be visible to the users 12a, 12b due to the overlayment of soft tissue including a dermal layer 14a of the patient. Because portions of the instruments 66a, 66b, are not viewable by the users 12a, 12b, the users may view the display device 20, as illustrated in FIG. 2B, to visualize and understand a location of the instruments 66a, 66b, relative to the vertebra 104. The determination of the location of the instruments 66a, 66b relative to the vertebra 104 is based upon the tracking of the respective tracking devices 68a, 68b and the determination of the location of the instruments 66a, 66b, as discussed above. It is understood, while the following discussing is directly to exemplarily including the two operative portions to both be tapping portions 102, that the operative portions may be different. The portions that may be manipulated, e.g. handles of the instruments 66a, 66b, however may be substantially identical. Further, it is understood that both or more of the instruments 66a, 66b may be manipulated by a single user, such as with both hands. In this instance, a distinguishing display, as discussed herein, may still allow for efficient identification of the tracked and displayed instrument.

The first instrument 66a may include the first tracking device 68a and/or 70a. As is understood in the art, the optical tracking device 68a may be tracked with the optical localizer 60, while the electromagnetic tracking device 70a may be tracked with the electromagnetic localizer 62. The following discussion is directed to the optical tracking device 68a, unless specifically indicated otherwise. However, it is understood that tracking the location of an instrument and determining its location relative to a portion, such as the vertebra 104, are substantially similar save for the type of tracking process and need not be repeated for various types of tracking system. The second instrument 66b may include the second optical and tracking device 68b and/or the second EM tracking device 70b. The instruments 66a, 68b may be calibrated relative to the navigation domain. Either the instrument may be precalibrated and the processor 26 may recall from the memory system 23, or any appropriate memory system, a distance of the distal tip of the respective tapping portions 100a, 100b, or the instrument with the respective tracking devices 68a, 68b may be touched to a known location (e.g. the patient tracker 64) within the navigation domain to calibrate the distance between the respective tracking devices 68a, 68b and the respective distal tips of the tapping portions 100a, 100b. In one example, the localizer 60 may include within a field of view the patient tracker 64 and the respective tracking devices 68a, 68b, thus the localizer can track the two instruments 66a, 66a substantially simultaneously with the patient tracker 64 for calibration and maintain registration during a procedure. The processor 26 can then determine the location of the distal tip of the tapping portions 100a, 100b relative to the respective tracking devices 68a, 68b and then the vertebra 104. The location of the vertebra 104 can be determined based upon tracking the patient tracker 64.

Once calibrated, a first instrument icon 110a can be illustrated relative to the image data 18 including a reconstruction or raw image of the vertebra 104 as an image of the vertebra 104a' on the display 20. Similarly, a second icon 110b can be illustrated relative to an image or reconstruction of the vertebrae as the image or reconstruction 104b' on the display 20. Accordingly, the image data 18 can include at least two views of the acquired image data including a view of the instruments 66a, 66b as the first icon 110a and the second icon 110b, respectively.

With continuing reference to FIG. 2B, a left portion of the image data 18l may illustrate only the vertebra image 104a' and the first icon 110a representing the location of the first instrument 66a relative to the vertebra 104. The first instrument 66a may be positioned near a right pedicle of the vertebra 104 which is illustrated on the left side of the image data 18l. The image data may further include an indication regarding a perspective of the image, such as along a superior to inferior axis with an indication 116. Other indicia such as an "A" and a "P" may be illustrated to indicate anterior and posterior sides of the image. The image data 18 may also include a right hand side 18r that illustrates the vertebra 104b' including only a representation 110b of the second instrument 66b. The image data 18, including the image portions 18r and 18l may both be displayed on the display 20, which may be a single display. It is understood, however, that multiple displays may also be provided, as discussed herein. The second instrument 66b may be positioned near a left pedicle of the vertebra 104. The right image side 18r may also include an indication 118 regarding the direction of the image 18. The indication of 118 may also indicate that the image data is along a superior to inferior axis.

As illustrated in FIG. 2B, the two icons 110a and 110b, which are instrument icons, are substantially identical as they both represent tapping portions 110a and 100b of the respective instruments 66a and 66b. As the two instruments are substantially identical, the representations thereof in the image data 18 are also substantially identical. Accordingly, the two users 12a and 12b may use distinctions, as discussed herein, to more readily recognize which instrument the respective user 12a, 12b is holding.

To assist in identifying the specific instrument held by the respective user 12a or 12b when viewing the display device 20, an indication or distinction on the display device 20 in either the left image 18l or the right image 18r can be provided. The indication may be a user identifiable indication or indicia, as discussed herein. As discussed herein, the indicia may be a user viewable indicia, but the indicia may also be auditory, tactile, combinations therefore, etc. The user viewable indicia may be part of a user interface (UI) such as a graphical UI. The GUI may be customized based on the selected indicia, as discussed herein.

For example, as illustrated in FIG. 2B, the user viewable indicia may include an exterior portion, such as a border 120, can surround the left image 18l. The border 120 can have a feature such as a color, a pattern, a flash or blinking rate, or other indicia that correspond to a first tracking device indicia 122 on the first tracking device 68a. The first tracking device indicia may also be a user viewable indicia, as discussed below. Further, the first tracking device indicia may be a tactile or auditory indicia. For example, the border 120 can include a blue color and the first tracking device indicia 122 on the tracking device 68a can also be blue. Therefore, the first tracking device indicia 122 of the first tracking device 68a can match the color of the border 120 of the left image portion 18l. Therefore, the user 12a may view the first tracking device 68a, see the first tracking device indicia 122 and then view the display 20, see the color of the border 120 and understand that the icon 110a relates to the first instrument 66a.

In a similar manner, the right image data 18r can include a user identifiable or viewable indicia such as a second border 124 that includes a second indicia such as a color, a pattern, a blink rate, or the like that matches a second tracking device indicia 126 of the second tracking device 68b. The second tracking device indicia 126 may be similar to the first racking device indicia 124, such as a color, tactile, auditory, etc. For example, the border 124 can include a gold color and the second tracking device indicia 126 may also be gold. Therefore, the second user 12b may view the second tracking device 68b, see the second tracking device indicia 126 and then view the order 124 of the right image data 18r on the display device 20 and understand that the second icon 110b represents the location of the second instrument 66b.

Accordingly, a visual indication, including the borders 120, 124 can be used to identify and understand which icon 110a, 110b relates to which of the instruments 66a, 66b. By matching the color of the borders 120, 124 with the respective tracking device indicia 122 to 126 a user may view the tracking device indicia and the visual distinction (i.e. the borders 120, 124) on the display 20 to understand which icon 110*a*, 110*b* relates to which instrument 66*a*, 66*b*. Other distinctions, such as those discussed herein, may also be used to distinguish one icon 110*a* from the other icon 110*b* relative to the instruments 66*a*, 66*b*.

The electromagnetic tracking device 70*a*, 70*b* may also include respective indicia including a third tracking device indicia 130 and a fourth tracking device indicia 132. The third and fourth tracking device indicia 130, 132 can be substantially identical to the first and second tracking devices indicia 122, 126. For example, the first tracking device indicia 122 and the third tracking device indicia 130 may both be blue color while the second tracking device indicia 126 and the fourth tracking device indicia 132 may be a gold color. The indicia 130, 132 may be the color of a housing that houses a coil, a tactile feature of a house, etc. Nevertheless, it is understood that the tracking device indicia may be different and that the system may provide the indicia on the display, including the borders 120, 124 relating to the indicia on the selected tracking devices.

According to various embodiments, the first tracking device 68*a* may include a plurality of trackable portions. The tracking portions may be any tracking portions such as passive reflective portions, acoustic members, active emitters (e.g., light emitting diodes), or other portions. In an exemplary embodiment, the plurality of tracking portions include four reflecting members including 140, 142, 144, and 146. In a similar matter the second tracking device 68*b* may include four tracking portions including four reflector members 150, 152, 154, and 156. The tracking portions 140-146 may be oriented in a specific geometry on the first tracking device 68*a*. The first geometry of the tracking portions 140-146 may be substantially unique to the first tracking device 68*a*. The first geometry of the first tracking portions 140-146 may be saved in the database on the memory system 23. During a procedure, such as based upon input from the respective users 12*a*, 12*b* or substantially automatically by tracking the tracking device 68*a*, the processor 26 may access the database stored on the memory system 23, such as by executing instructions, to identify the tracking device 68*a* based on the first unique geometry that is seen or tracked with the localizer 60. Once the tracking device 68*a* is identified, the indicia 122, such as a color, may be recalled as saved in the database relating to the first unique geometry. Once the first tracking device 68*a* is identified the border 120, as a part of a customized user interface (UI) can be changed to the appropriate instrument indicia to match the first tracking device indicia 122.

According to various embodiments, a user, including the users 12*a*, 12*b* or other appropriate users, may also input during a procedure the indicia 122. For example, user can use the user input 24 to input the indicia 122 during a procedure as it relates to a specific instrument, such as the tap portion 100*a*. Therefore, the user can input that the first specific geometry of the first tracking portions 140-146 as it relates to the indicia 122 and/or the portion 100*a*. Therefore, when the tracking system, including the localizer 60, identifies the first geometry based upon the tracking portions 140-146. The processor 26 may automatically form the border 12,0 including the appropriate indicia relating to the first tracking device indicia 122, including a selected color, based on the tracking device and the geometry thereof that is tracked. Therefore, the indicia 122 can be saved in a database to be accessed by the processor 26 or can be entered during a procedure by a user, including the users 12*a*, 12*b*. According to various embodiments, the According to various embodiments, the indicia 122, 126, 130, 132 can be provided as a signal directly from the tracking devices 68*a*, 68*b*, 70*a*, 70*b*. For example, a memory (such as a selected read-only-memory system) may be provided to transmit a signal, once interrogated, to the navigation system. For example, the coils of the EM tracking devices 70*a*, 70*b* may be used to transmit an indicia signal to the navigation system that identifies the respective indicia from a memory included within or in communication with the tracking devices 70*a*, 70*b*. Further, an indicator on the selected tracking device 68*a*, 68*b*, 70*a*, 70*b* may identify the indicia 122, 126, 130, 132. The indicator may include a radio frequency identification tag that includes a coil that may be interrogated and then emits a signal. The indicator may also or alternatively be an optical code (e.g. a bar code, two dimension codes readable by a QR Code® scanner, etc.) that is read by an appropriate optical reader. Thus, the navigation system may automatically receive a signal that includes the information for displaying the distinguishing features (e.g. icons 11*a*', 110*b*') on the display 20. Accordingly, one skilled in the art will understand that a database or lookup table is not required, but that information identifying the indicia 122, 126, 130, 132 may be provided directly with the tracking devices for receipt by a signal to the navigation system for display on the display device 20 to customize the UI, which may be a graphical user interface.

In a similar manner, the second tracking device 68*b* can have a second specific geometry or unique geometry based upon the tracking portions 150-156. Accordingly, in a similar manner, upon tracking or input by the user, the tracking system, including processor 26, can automatically generate the border 124 to customize the UI to match or correlate to the second tracking device indicia 126. Again, the tracking portions 150-156 can be any appropriate tracking portions, including those discussed above, and can be identified by the tracking systems substantially automatically or by input of a user.

By an appropriate process, the UI on the display 20 is customized to distinguish the first instrument 66*a* relative to the first icon 110*a* and the second instrument 66*b* to the second icon 110*b*. The UI may include the borders 120, 124 displayed relative to the image data portions 18*l* or 18*r* corresponding to the respective instruments 66*a*, 66*b* being illustrated by the icons 110*a* or 110*b*. Thus, the respective users 12*a*, 12*b* may visually identify in a substantially efficient manner the portion of the image data 18 and the respective icons 110*a*, 100*b* that relates to the specific instruments 66*a*, 66*b*. The users 12*a*, 12*b* may then understand the location of both the instruments 66*a*, 66*b* relative to the patient 14 substantially simultaneously.

Again, it is understood that the electromagnetic tracking devices 70*a*, 70*b*, may include respective tracking device indicia 130, 132. The respective tracking device indicia may include a user identifiable or distinguishable features such as a viewable feature (e.g. color of a coil housing), tactile or auditory feature. The tracking system may distinguish between the tracking devices 70*a*, 70*b*, and therefore, the respective instruments 66*a*, 66*b*, based upon a signal from the respective tracking devices 70*a*, 70*b*. The respective tracking devices 70*a*, 70*b* may either transmit and/or receive an electromagnetic signal, which may include a unique signal that is correlated to a specific tracking device. Therefore, the processor 26 may again execute appropriate instructions to generate the customized UI, including the respective borders 120, 124 relating to the respective instruments 66*a*, 66*b* depending on the specific tracking devices 70*a* or 70*b* associated therewith.

Figure 3A:
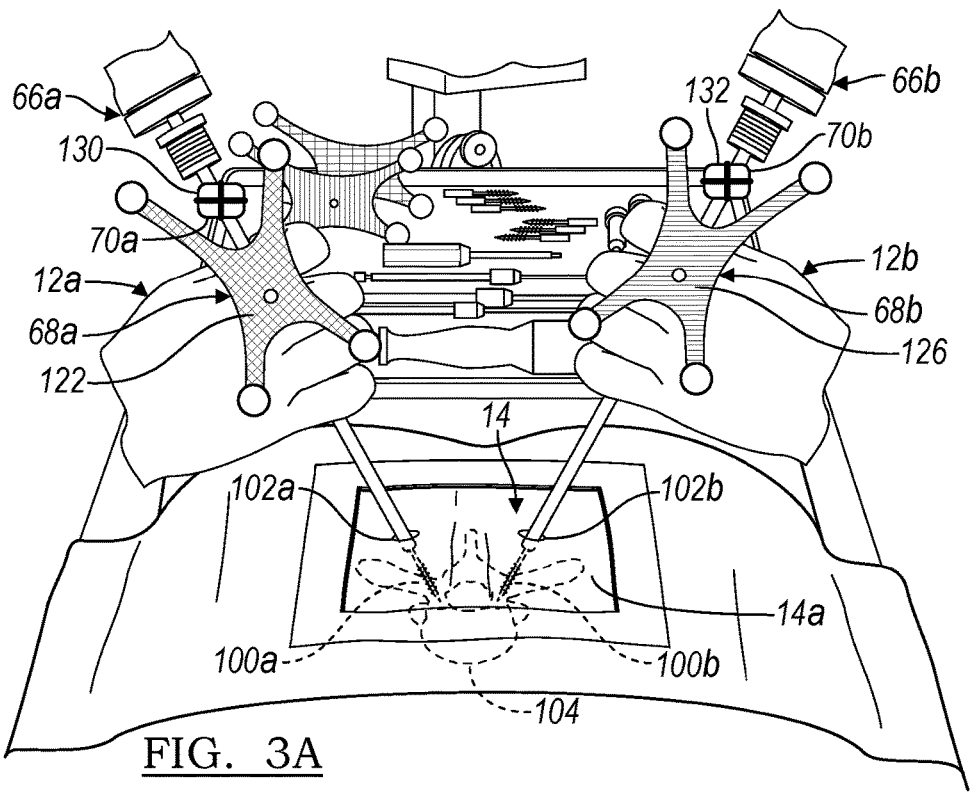
FIG. 3A is an environmental view of a procedure occurring with two instruments, according to various embodiments.
Figure 3B:
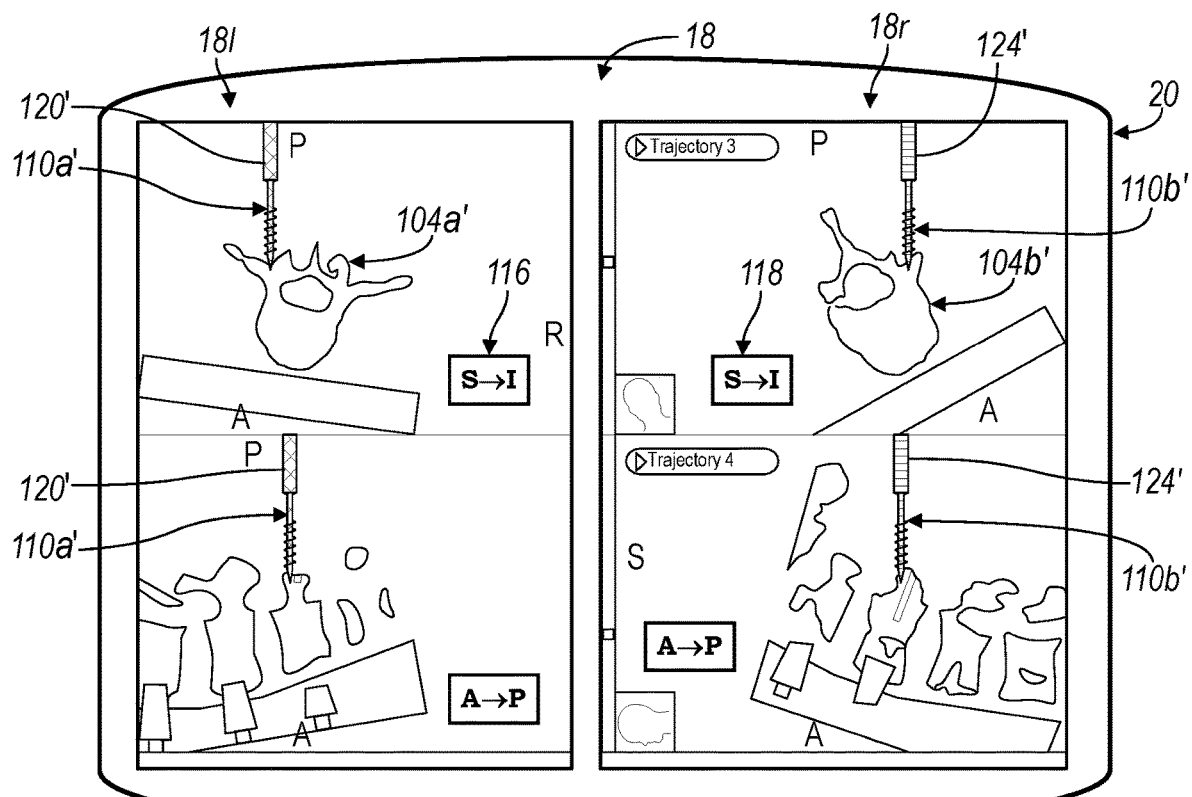
FIG. 3B is a screenshot of a display device displaying the two instruments with a visual distinction, according to various embodiments.

Turning reference to FIGS. 3A and 3B, the instruments 66*a* and 66*b* are illustrated relative to the patient 14 in FIG. 3A in a manner substantially similar to that illustrated in FIG. 2A. Again, the instrument 66*a* and 66*b* include the respective tracking devices 68*a*, 68*b* and/or 70*a*, 70*b*. Again, it is understood that only a single type tracking device may be required for attachment or inclusion with the instruments, but the two illustrated for exemplary purposes. Further, each of the tracking devices 68*a*, 68*b* they include respective tracking device indicia 122 and 126. Each of the instruments 66*a* and 66*b* may include operating or manipulating portions, such as tapping portions 100*a*, 100*b*. The tapping portions 100*a* and 100*b* may be hidden from direct view of the respective users 12*a*, 12*b* due to the dermal layer 14*a* of the patient 14. Accordingly, the users 12*a*, 12*b* may view the display device 20 to understand a location of the instruments 66*a* and 66*b* relative to the patient 14, including the vertebra 104.

Accordingly, with reference to FIG. 3B, the left image data portion 18*l* may include a first instrument icon 110*a'* that includes a first indicia 120'. The first indicia 120' may, again, be a user identifiable indicia including a user viewable color on the display 20, a sound, a tactile feature, etc. The first indicia 120' may be substantially limited to the icon 110*a'*. As discussed above, the indicia border 120 may include a blue color, and the first indicia 120' may also include the blue color. Accordingly, the icon 110*a'* may be colored blue to include the indicia 120'. Again, the first tracking device indicia 122 of the first tracking devices 68*a* may be blue. The first user 12*a* holding the instrument 66*a* that includes the first tracking device 68*a* may view the blue color of the first tracking device indicia 122 on the instrument 66*a* and then or substantially simultaneously view the blue color of the icon indicia 120' on the display device 20. Similarly, the second user 12*b* holding or manipulating the second instrument may view the second tracking device indicia 126 and then view a second icon indicia 124' of the second instrument icon 110*b'*. The second indicia 124' may, again, be a user identifiable indicia including a user viewable color on the display 20, a sound, a tactile feature, etc. The second icon indicia 124' may be substantially similar to the tracking device indicia 124 including a gold color, as discussed above. It is understood, however, that any appropriate color may be used to correlate or match between the icon indicia 120' and 124' and the tracking device indicia 122 and 126.

The illustration of the instrument indicia 120' and 124' can again be based upon identification of a unique geometry of tracking portions of the respected tracking devices 68*a*, 68*b*, as discussed above, or a unique signal of the respective tracking device 70*a*, 70*b*, also as discussed above. Further, as also as discussed above, the user may input into the system, the respective indicia using the input device 24. Nonetheless, the respective users 12*a*, 12*b* can view the tracking device 68*a* and 68*b* and the respective tracking device indicia 122 and 126 and then or substantially simultaneously view the display device 20 to identify the icon 110*a'* and 110*b'* based upon the icon indicia 120' and 124' as relates to the respective instrument 66*a* or 66*b*. Therefore, the users 12*a*, 12*b* can more readily identify the icon 110*a'* or 110*b'* on the display device 20 that relates to the first instrument 66*a* or the second instrument 66*b* in the patient space or real space. This can allow the users to identify and properly orient their respective movements of the respective instruments 66*a*, 66*b* relative to those of icons on the display device 20.

Figure 4A:
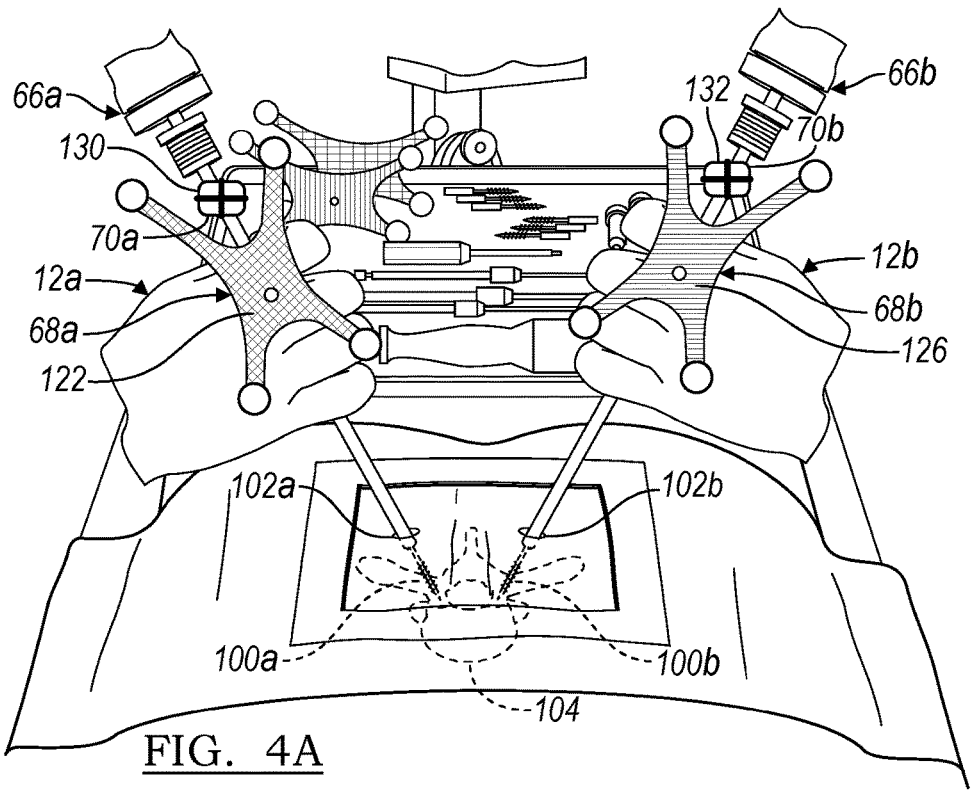
FIG. 4A is an environmental view of a procedure occurring with two instruments, according to various embodiments.
Figure 4B:
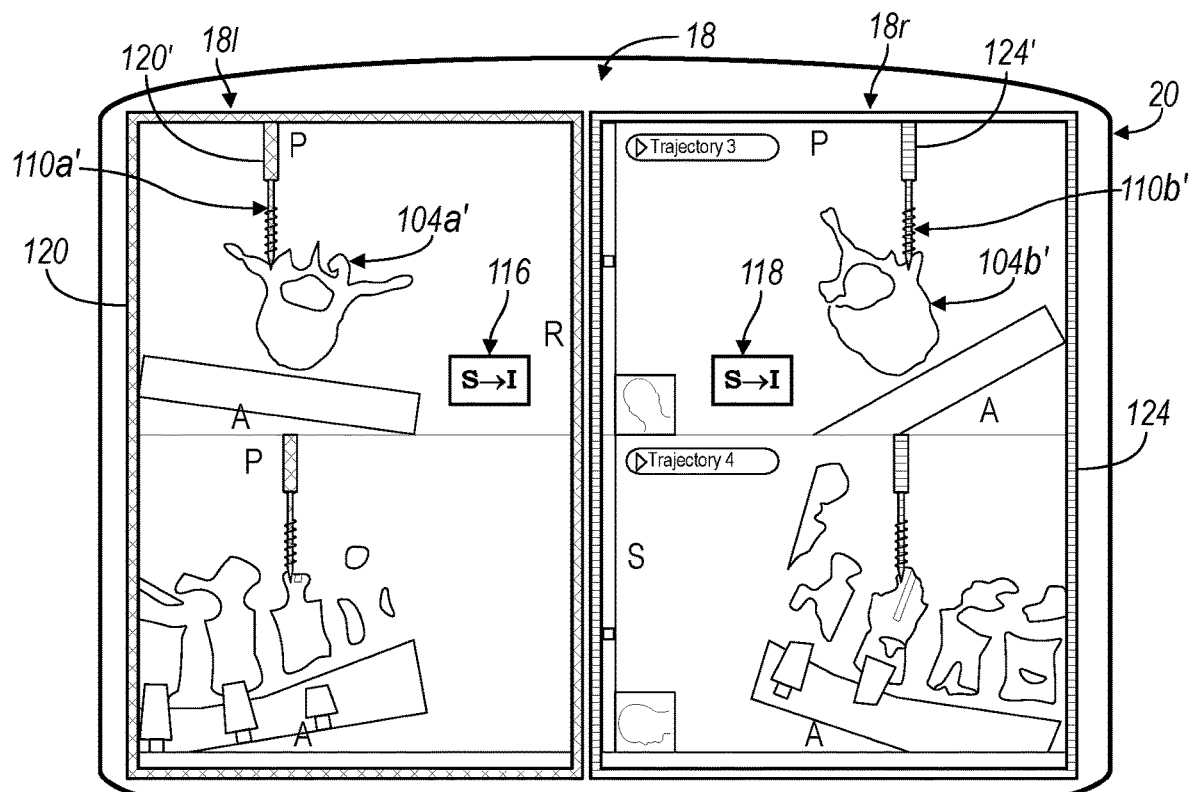
FIG. 4B is a screenshot of a display device displaying the two instruments with a visual distinction, according to various embodiments.

With reference to FIGS. 4A and 4B, the instruments 66*a* and 66*b* including the respective tracking devices 68*a*, 68*b* and/or 70*a*, 70*b* are illustrated relative to the patient 14 in a manner similar to that illustrated in FIGS. 2B and 3B. Accordingly, each of the tracking devices 68*a* and 68*b* may include respective tracking device indicia 122 and 126. Further, the tracking devices 68*a* and 68*b* each have unique geometries, such as the first unique geometry of the first tacking device 68*a* and the second unique tracking device 68*b* based upon the tracking portions thereof, as discussed above. The tracking system when tracking the respective tracking devices 68*a* and 68*b* can identify the respective first and second unique geometries and then the respective tracking device indicia 122 and 126 can be recalled or determined, as discussed above. The UI can then be customized based on the indicia 122, 126 and can be displayed relative to the respective left image portion 18*l* and the right image portion 18*r*.

As illustrated in FIG. 4B the left image data portion 18*l* may include both the border indicia 120 and the icon indicia 120' of the first instrument icon 110*a'*. Further, the right image data portion 18*r* can include the border indicia 124 in combination with the icon indicia 124' of the second instrument icon 110*b'*. Therefore, user may view both the border and/or the respective icons to correlate the image data portion, either 18*l* or 18*r*, relating to the respective instruments 66*a* and 66*b*. The indicia, on the display device 20, can be provided in a manner substantially similar to that discussed above in relation to FIGS. 2B and 3B, and need not be repeated here.

It is further understood that a plurality of display devices may be provided. For example, a second display device 20' may also display the image data, as image data 18'. The second display device 20' may be in position away from the display device 20 within the operating theater 10 that is more convenient for viewing one or more users, such as the user 12*b*. The second display device 20' may be connected via a connection 150 with the computer system 22 to display a display substantially similar to the display on the display device 20. According to various embodiments, however, the display 20 may display a different image than the display 20'. For example, the display 20 may display only the image portion 18*l* while the second display 20' may display only the image portion 18*r*. As discussed in relation to FIGS. 2B to 4B, the respective image portions 18*l*, 18*r* can include the indicia related to the respective tracking devices 68*a*, 68*b* for correlating to the respective instruments 66*a* and 66*b* such that the users 12*a*, 12*b* can readily identify the image and superimposed icons (i.e. 110*a*, 110*b*, 110*a'*, 110*b'*) relating to the instruments manipulated by the respective users. Generally understood graphic protocols can be used to provide the image portions to respective displays based upon an input from the user. The user input is understood to include direct user input or based upon direction of a user.

Further, the user 12*a* may select to view the respective image portion at a different orientation then the user 12*b*. Accordingly, the second user 12*b* may desire to view the image portion, for example, the image portion 18*r* from an inferior to a superior orientation. The user 12*a*, 12*b* may input to the selection and the image 18*r* may then be displayed along the appropriate axis. The inclusion of the respective indicia, such as the indicia 120, 120' and 124, 124', may allow the respective user to readily identify the instrument manipulated by the respective user and understand the orientation of the image data being viewed relative to the tracked instrument 66*a*, 66*b* so that the user that identified a selected orientation of the image portion may better understand the position of the instrument relative to the patient 14.

Further, the tracking system including the respective single optical localizer 60 or the single localizer 62 can track instruments at various locations relative to the patient 14. For example, the first instrument 66a may be positioned relative to a first vertebra, such as L5, while the second instrument 66b may be positioned relative to a different vertebra, such as L4. The respective image data portion 18l or 18r may, therefore, illustrate different vertebrae, such as the L5 vertebra or the L4 vertebra, and the respective display indicia 120, 120', 124, 124' can be illustrated on the display device 20 substantially simultaneously relative to the appropriate vertebra for viewing by the respective users 12a, 12b operating on the respective vertebra. Accordingly, the single display device 20 may substantially simultaneously display two portions of an operation occurring substantially simultaneously, as discussed further herein, even if not on a rigidly connected boney portion. In a further example, the first instrument 66a may be tracked and illustrated relative to a spine while the second instrument 66b is tracked and illustrated relative to a femur.

Figure 5:
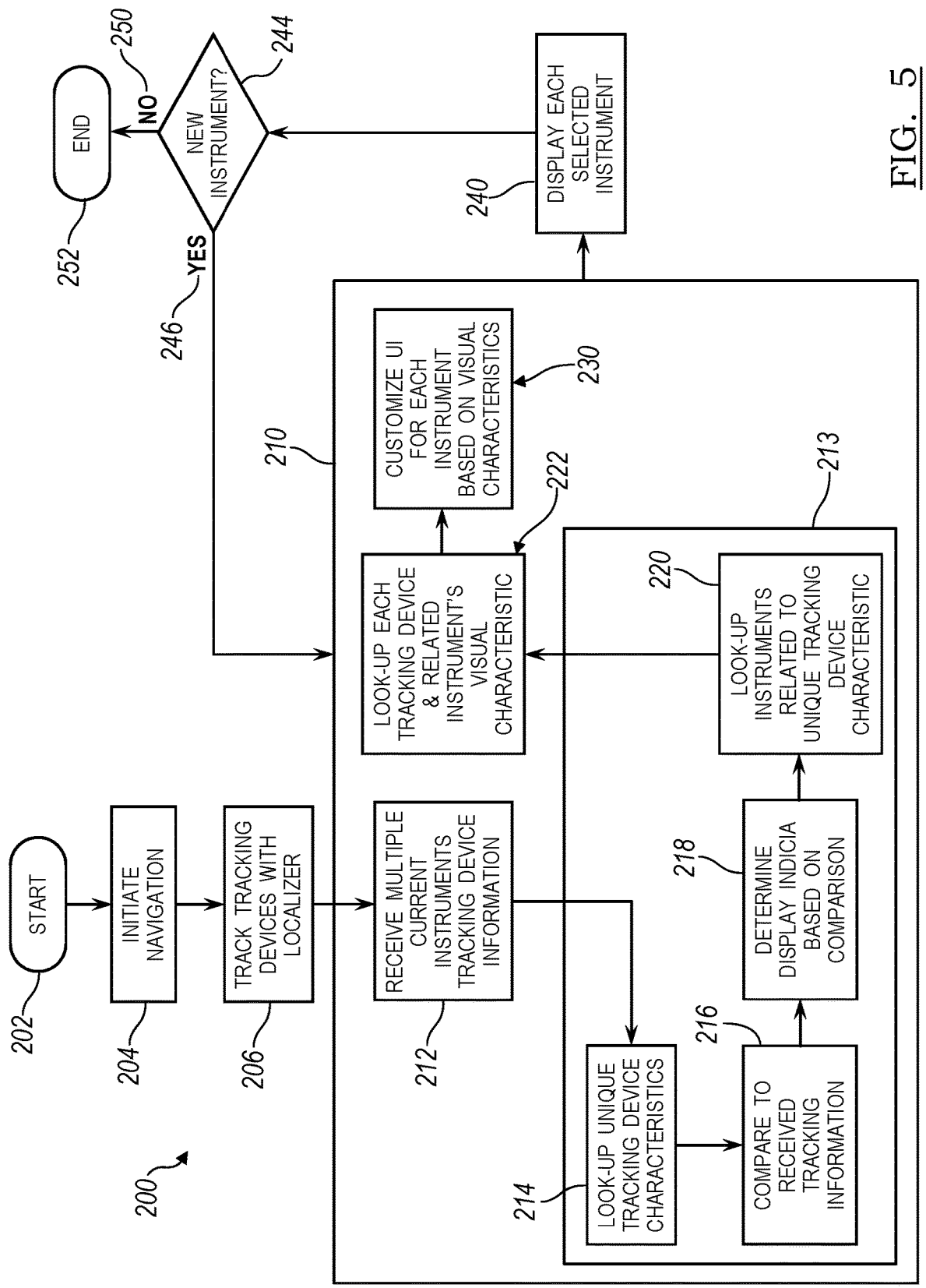
FIG. 5 is a flowchart illustrating various portions of a method to illustrate two instruments distinctly.

Turning reference to FIG. 5, a flowchart 200 is illustrated. As illustrated, the flowchart 200 may be incorporated into computer instructions that may be executed by the processor 26 for generating the display including the UI and the image data for display on the display device 20 and/or 20', as discussed above. Accordingly, it is understood that the flowchart 200 may represent the steps of computer software incorporated into computer system or instructions for the processor 26 for generating the display on the display device 20 and/or 20'.

The flowchart 200 can begin in a start block 202, the method may then progress to block 204 where navigation is initiated. Navigation being initiated according to various procedures, such as activation of the navigation system by the users 12a, 12b, positioning a trackable instrument within the navigational domain, or other appropriate steps. Nevertheless, initiation of navigation may include tracking or receiving tracking information regarding one or more of the tracking devices 68a, 68b, or other appropriate tracking devices.

After initiating navigation of block 204, the localizer may be used to track the instruments in the track with localizer block 206. The localizer can be used to track the tracking device according to generally known tracking systems and techniques, so that the navigation system can determine the location of the tracked instruments, such as the instruments at 66a and 66b relative to the patient 14 for display on the display device 20. The localizer can then forward the tracking information to the processor 26 for execution of a routine 210 to generate the display on the display device 20. The localizer can forward or transmit the information including raw data regarding a visual orientation of the tracking devices 68a and 68b or field strength determined with the electromagnetic tracking devices 70a and 70b or processed data regarding the tracking devices. Nevertheless, the tracking device information from the localizer based upon tracking the tracking devices with the localizer in block 206 can be forwarded to the computer 22 for operation according to the routine 210.

Initially the multiple tracked instruments, including the instruments in 66a and 66b, can be received in block 212. The tracking information can be based upon tracking the tracking portions of the tracking devices 68a and 68b or the respective unique signals from tracking devices 70a and 70b. Regardless of the tracking information received in block 212, the localizer, including localizer 60, can receive the plurality tracking information regarding all of the tracking devices in the navigation domain. Accordingly, the tracking devices may also include the patient tracker 64.

After receiving the tracking information of block 212, an optional sub-routine 213 may be entered that includes a look-up of unique tracking characteristics can be made in block 214. As noted above, the tracking devices, including the tracking devices 68a and 68b can include specific unique geometries based upon the tracking portions thereof. The unique geometries to be saved as unique tracking device characteristics in a look-up table or database, which may then be accessed in look-up unique tracking device characteristics in block 214. Also as noted above, the unique tracking device characteristics can include specific signals, information and other distinct characteristics relating to a single tracking device, including the electromagnetic devices 70a and 70b. Further, the unique tracking device characteristics can include the tracking device indicia including the indicia 122, 126, 130, and 132, including the features as discussed above.

The look-up table can include a correlation or a match between the specific tracking information characteristic and the indicia based upon the specific tracking device and the received multiple tracking device information from block 212. In block 216, the received tracking information from block 212 can then be compared to the look-up unique tracking device characteristics in block 214. After comparing the received tracking information in block 216 a determination of display indicia based on the comparison can be made in block 218. For example, as noted above, the tracking information relating to the tracking device 68a can be received in block 212 and the look-up in block 214 can be made of possible tracking devices and the comparison in block 216 can identify the unique geometry of the tracking device 68a and the first tracking device indicia 122 thereof.

A determination for displaying the indicia in block 218 can be a determination in displaying the blue indicia, as noted above. Following a determination of the displaying indicia based on the comparison in block 218, a look-up of the instrument related to the unique tracking device characteristic can be made in block 220. As noted above, the various tracking devices, including the tracking in 68a and 68b can be connected to two different selected instruments which may be varied between procedures and even intra-procedurally. Accordingly, a look-up of the instrument attached to the specific tracking device can be made in block 220.

The sub-routine 213 is optional, and need not be required. Therefore, either directly from receiving the tracking information in block 212 or after the look-up of instruments in block 220, a look-up of the tracking device and instrument's visual characteristics can be made in block 222. The instruments visual characteristics can include a specific icon, including the icons 110a and 110b which represent a tapping portion, for display on display 20, such as superimposed on the image data 18. It is also understood that the visual characteristics may include an icon to represent an awl, an icon to represent a screw, etc., and the various geometries and dimensions thereof.

After the look-up of the instruments visual characteristics in block 222, based upon the look-up of the related instrument in block 220, a determination of a customized UI for each instrument based upon its visual characteristics can be made in block 230. In customizing the UI, the system selects the appropriate icon to be displayed, including the icons

110*a* or 110*b* that relate to the visual characteristics of the instrument looked up in block 222. Further, the customization of the UI can include determination of the display indicia from block 218. As noted above, the display indicia can include the border 120 or 124 and/or the icon indicia 120' or 124', or other appropriate distinction indicia.

After the UI is customized in block 230, a selected display may be generated based upon or during customization of the UI. The routine 210 may then be exited and a display of each selected instrument is made in block 240. As discussed above, the display device 20 can display the respective icons, including the icons 110*a* and 110*b*, and the respective indicia including the border indicia 120 and 124 and the icon indicia 120' and 124'. Further, as discussed above, the display device 20 and the UI thereon may not display all tracked portions in the navigational domain. As discussed above, the patient tracker 64 may not be displayed or selected to be displayed on the display device 20. Accordingly, when displaying the instruments as icons of a display device 20, it can be selected to not display selected portions, such as the patient tracker 64 or other trackable portions.

After the display of the customized UI is made in block 240, a determination in block 244 can be made of whether a new instrument has been input or identified with the received tracking information in block 212. If the determination is yes, such as based upon tracking a new unique tracking device or input from a user, a YES routine in block 246 can be followed to re-enter the routine 210. Accordingly, the display on the display device 20 can be updated when a new instrument that is placed in the navigational domain. The update may be either automatic based upon tracking a new instrument or based upon input from a user. However, if no instrument is identified then a NO routine can be followed in block 250 to end block 252. The end block 252 may be simply continuing to track the selected instruments and displaying them on the display device 20 based upon movements of the user of the respective instruments 66*a* and 66*b*, but may also include ending the procedure.

The system described above can allow for the display of a plurality of instruments on the display device 20, 20' relative to the image data 18, 18' with unique identifying characteristics for each of the displayed instruments based upon identifiable characteristics of at least the respective tracking devices, including the tracking devices 68*a* and 68*b* connected through the respective instruments 66*a* and 66*b*. The identifying characteristics can allow for a plurality of surgical steps to occur substantially simultaneously, as discussed above, with a plurality of users.

For example, during positioning of an implant for spinal fusion, pedicle screws can be placed contralateral, i.e. on both a left and right portion of a vertebra. When only a single instrument is displayed on the display device 20 the procedure, if navigated, may only occur for positioning a single screw at a time. Accordingly, each navigated step for positioning the screw must be performed in sequence. Each step for positioning a screw may include identifying a trajectory, forming a bore in a vertebra, tapping into the bore, and positioning the screw in the tapped bore. This sequence of steps must be repeated twice for each vertebra in which screws will be positioned. However, when two instruments may be distinguishable on the display device 20, the two users 12*a* and 12*b* may both perform the sequence of steps for positioning pedicle screw in a vertebra together or substantially simultaneously.

It is further understood that more than two instruments may be illustrated substantially simultaneously on the display device 20 or on a plurality of display devices including the display devices 20' and 32*a*. When more than two instruments are visually distinguishable more than two users may perform surgical steps or steps of any appropriate procedures substantially simultaneously and be able to visually distinguish the tracked instrument based upon on an indicia relating to each of the tracking devices positioned on the respective instruments.

Further, it is understood that a kit 300 may include more than two indistinguishable tracking devices. Returning reference to FIG. 2A, the kit 300 may include a third tracking device 68*c* and a fourth tracking device 68*d*. Each of the third and fourth tracking devices 68*c* and 68*d* may include respective third and fourth unique geometries that are different than any of the other geometries including the first and second unique geometries. Further, the tracking devices 68*c*, 68*d* would also include third and fourth tracking device indicia different than the first and second tracking device indicia. These indicia may also be incorporated into the UI to assist in distinguishing the displayed icons representing the instruments. It is also understood that plurality of electromagnetic tracking devices also provided to be tracked substantially simultaneously. Each of the tracking devices can be connected to unique instrument that can be tracked on the navigational domain to be illustrated substantially simultaneously on selected displayed devices for viewing by appropriate users.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, various embodiments are disclosed herein. Although each of the embodiments are described as having certain features, any one or more of the features described with respect to any one embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The wireless communications described in the present disclosure can be conducted in full or partial compliance with IEEE standard 802.11-2012, IEEE standard 802.16-2009, IEEE standard 802.20-2008, and/or Bluetooth Core Specification v4.0. In various implementations, Bluetooth Core Specification v4.0 may be modified by one or more of Bluetooth Core Specification Addendums 2, 3, or 4. In various implementations, IEEE 802.11-2012 may be supplemented by draft IEEE standard 802.11ac, draft IEEE standard 802.11ad, and/or draft IEEE standard 802.11ah.

Connections and/or relationships between elements (including circuit elements, non-circuit elements, modules, etc.) are described using various terms, including "connected," "engaged," "coupled," "adjacent," and "disposed." As an example, when a connection between first and second elements is described in the above disclosure, that connection can be a direct connection where no other intervening elements are present between the first and second elements, but can also be an indirect connection where intervening elements are present between the first and second elements. Other words used to describe a relationship between elements should be interpreted in a similar manner (e.g., "engaged" versus "directly engaged", "coupled" versus "directly coupled", etc.). When a first element is adjacent to a second element, the first element may be in contact with the second element or the first element may be spaced away from the second element without any intervening element between the first element and the second element. When a first element is between a second element and a third element, the first element may be directly connected to the second element and the third element (referred to as "directly between") or intervening elements may be connected (i) between the first element and the second element, and/or (ii) between the first element and the third element. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A method of distinguishing two tracked instruments, comprising:
    determining a first tracking device characteristic of a first tracking device associated with a first instrument;
    determining a second tracking device characteristic of a second tracking device different from the first tracking device associated with a second instrument;
    looking up in a first database a first tracking device indicia of the first tracking device, wherein the first tracking device indicia is user distinguishable;
    looking up in a second database a second tracking device indicia of the second tracking device, wherein the second tracking device indicia is user distinguishable from the first tracking device indicia;
    customizing a user interface to illustrate a first icon including a first icon indicia based on the first tracking device indicia and a second icon including a second icon indicia based on the second tracking device indicia; and
    displaying the customized user interface associated with the first tracking device and the second tracking device;

wherein customizing the user interface to illustrate the first icon including the first icon indicia based on the first tracking device indicia includes forming the first icon to include a first color that matches a first color of the first tracking device indicia in only a first image;
wherein customizing the user interface to illustrate the second icon including the second icon indicia based on the second tracking device indicia includes forming the second icon to include a second color that matches a second color of the second tracking device indicia in only a second image;
wherein the first and second images are simultaneously displayed.

2. The method of claim 1, further comprising:
superimposing the customized user interface over image data.

3. The method of claim 2, further comprising:
tracking a first location of the first tracking device;
tracking a second location of the second tracking device;
wherein superimposing the customized user interface over image data is based on the tracking of the first tracking device and tracking of the second tracking device.

4. The method of claim 3, further comprising:
maintaining a registration of the image data by tracking a third tracking device connected to a portion imaged in the image data.

5. The method of claim 1, further comprising:
determining a third tracking device characteristic of a third tracking device associated with a third instrument;
looking up in a third database a third tracking device indicia of the third tracking device;
changing the customized user interface to illustrate a third icon including a third icon indicia based on the third tracking device indicia; and
displaying the changed customized user interface.

6. The method of claim 1, further comprising:
determining a third tracking device characteristic of a third tracking device associated with at least one of the first instrument or the second instrument;
looking up in a third database a third tracking device indicia of the third tracking device;
changing the customized user interface to illustrate a third icon including a third icon indicia based on the third tracking device indicia that replaces at least one of the first icon or the second icon; and
displaying the changed customized user interface.

7. The method of claim 1, further comprising:
providing the first database and the second database as a single database accessible by a processor system.

8. The method of claim 1, further comprising:
generating a first signal based on tracking the first tracking device and a second signal based on tracking the second tracking device;
wherein determining the first tracking device characteristic of the first tracking device is based on the first signal;
wherein determining the second tracking device characteristic of the second tracking device is based on the second signal.

9. The method of claim 8, wherein the first signal includes a first unique geometry of first tracking portions of the first tracking device and the second signal includes a second unique geometry of second tracking portions of the second tracking device.

10. The method of claim 1, further comprising:
tracking the first instrument having the first tracking device;
tracking the second instrument with the second tracking device;
wherein displaying the customized user interface includes displaying both the first icon and the second icon on a display device simultaneously.

11. A method of distinguishing two tracked instruments, comprising:
determining a first tracking device characteristic of a first tracking device associated with a first instrument;
determining a second tracking device characteristic of a second tracking device different from the first tracking device associated with a second instrument;
looking up in a first database a first tracking device indicia of the first tracking device, wherein the first tracking device indicia is user distinguishable;
looking up in a second database a second tracking device indicia of the second tracking device, wherein the second tracking device indicia is user distinguishable from the first tracking device indicia;
customizing a user interface to illustrate a first icon including a first icon indicia based on the first tracking device indicia and a second icon including a second icon indicia based on the second tracking device indicia; and
displaying the customized user interface associated with the first tracking device and the second tracking device;
wherein customizing the user interface to illustrate the first icon including the first icon indicia based on the first tracking device indicia includes forming a first border to be displayed around a first image to have a first color that matches a first color of the first tracking device indicia to display only the first icon in the first image;
wherein customizing the user interface to illustrate the second icon including the second icon indicia based on the second tracking device indicia includes forming a second border to be displayed around a second image to have a second color that matches a second color of the second tracking device indicia to display only the second icon in the second image.

12. The method of claim 11, wherein customizing the user interface to illustrate the first icon including the first icon indicia based on the first tracking device indicia further includes forming a first border to be displayed around the first image to have the first color that matches the first color of the first tracking device indicia;
wherein customizing the user interface to illustrate the second icon including the second icon indicia based on the second tracking device indicia includes forming a second border to be displayed around the second image to have the second color that matches the second color of the second tracking device indicia.

13. A method of distinguishing two tracked instruments, comprising:
associating a first tracking device with a first instrument;
associating a second tracking device different from the first tracking device with a second instrument;
operating a processor system configured for:
determining a first tracking device characteristic of the first tracking device,
determining a second tracking device characteristic of the second tracking device;

customizing a user interface to visually distinguish a first icon representing the first instrument and a second icon representing the second instrument; and operating a display device to display the customized user interface to visually distinguish the first icon and the second icon displayed on the display device and associated with the first tracking device and the second tracking device;

wherein customizing the user interface to illustrate the first icon based on the first tracking device includes forming the first icon to include a first color that matches a first color of the first tracking device in only a first image;

wherein customizing the user interface to illustrate the second icon based on the second tracking device includes forming the second icon to include a second color that matches a second color of the second tracking device in only a second image; and wherein the first and second images are simultaneously displayed.

14. The method of claim 13, further comprising:

operating a tracking system to simultaneously track the first instrument and the second instrument with the first tracking device and the second tracking device.

15. The method of claim 14, further comprising:

operating the first instrument and the second instrument substantially simultaneously for at least one of forming contralateral bores in a single vertebra, tapping formed contralateral bores, inserting screws in tapped contralateral bores;

wherein operating the first instrument and the second instrument substantially simultaneously is based at least in part on visualization provided by the first icon and the second icon displayed on the display device.

16. The method of claim 14, further comprising:

operating the first instrument and the second instrument substantially simultaneously for at least one of forming two bores, tapping two formed bores, inserting screws in two tapped bores;

wherein operating the first instrument and the second instrument substantially simultaneously is based at least in part on visualization provided by the first icon displayed in a first image having a first portion of a patient and the second icon displayed in a second image having a second portion of the patient on the display device.

17. The method of claim 13, wherein determining the first tracking device characteristic of the first tracking device includes providing a first input to the processor system to define the first tracking device characteristic;

wherein determining the second tracking device characteristic of the second tracking device includes providing a second input to the processor system to define the second tracking device characteristic.

18. The method of claim 13, wherein customizing the user interface to visually distinguish the first icon and the second icon is selected from the group consisting of forming a first border different from a second border, coloring the first icon different from the second icon, and both forming the first border different from the second border and coloring the first icon different from the second icon.

* * * * *

UNITED STATES PATENT AND TRADEMARK OFFICE
CERTIFICATE OF CORRECTION

| | |
|---|---|
| PATENT NO. | : 11,744,649 B2 |
| APPLICATION NO. | : 17/116050 |
| DATED | : September 5, 2023 |
| INVENTOR(S) | : Justin Kemp et al. |

It is certified that error appears in the above-identified patent and that said Letters Patent is hereby corrected as shown below:

In the Specification

Column 4, Detailed Description, Line 21, Delete "Cl" and insert --C1-- therefor

Column 4, Detailed Description, Line 26, Delete "Cl" and insert --C1-- therefor

Column 6, Detailed Description, Line 18, Delete "be be" and insert --be-- therefor Column 6, Detailed Description, Line 20, Delete "used" and insert --user-- therefor Column 7, Detailed Description, Line 38, Delete "66a, 66a" and insert --66a, 66b-- therefor Column 7, Detailed Description, Line 56, Delete "181" and insert --18l-- therefor Column 7, Detailed Description, Line 61, Delete "181." and insert --18l.-- therefor Column 8, Detailed Description, Line 2, Delete "181" and insert --18l-- therefor Column 8, Detailed Description, Line 8, After "indication", delete "of"

Column 8, Detailed Description, Line 23, Delete "181" and insert --18l-- therefor Column 8, Detailed Description, Line 33, Delete "181." and insert --18l.-- therefor Column 8, Detailed Description, Line 44, Delete "181." and insert --18l.-- therefor Column 8, Detailed Description, Line 55, Delete "racking" and insert --tracking-- therefor Signed and Sealed this
Eighth Day of October, 2024

Katherine Kelly Vidal
*Director of the United States Patent and Trademark Office*